(12) United States Patent
Allum et al.

(10) Patent No.: US 11,229,767 B2
(45) Date of Patent: Jan. 25, 2022

(54) REMOTE OXYGEN FLOW ADJUSTMENT

(71) Applicant: Silverbow Development, LLC, San Ramon, CA (US)

(72) Inventors: Todd Allum, Livermore, CA (US); Gregory J. Kapust, San Ramon, CA (US)

(73) Assignee: Silverbow Development, LLC, San Ramon, CA (US)

( * ) Notice: Subject to any disclaimer, the term of this patent is extended or adjusted under 35 U.S.C. 154(b) by 697 days.

(21) Appl. No.: 15/870,808

(22) Filed: Jan. 12, 2018

(65) Prior Publication Data

US 2018/0200474 A1    Jul. 19, 2018

Related U.S. Application Data

(60) Provisional application No. 62/446,335, filed on Jan. 13, 2017.

(51) Int. Cl.
*A61M 16/20* (2006.01)
*G05D 16/06* (2006.01)
(Continued)

(52) U.S. Cl.
CPC ...... *A61M 16/209* (2014.02); *A61M 16/0003* (2014.02); *A61M 16/026* (2017.08);
(Continued)

(58) Field of Classification Search
CPC ............ A61M 16/209; A61M 16/0003; A61M 16/201; A61M 16/026; A61M 16/20;
(Continued)

(56) References Cited

U.S. PATENT DOCUMENTS

| 547,506 A | * | 10/1895 | Sleigh | ............... F16K 1/02 |
| | | | | 251/276 |
| 2,294,314 A | * | 8/1942 | McKinley | ......... G05D 16/0655 |
| | | | | 137/484.8 |

(Continued)

FOREIGN PATENT DOCUMENTS

| WO | 2011/049633 A2 | 4/2011 |
| WO | 2012/128870 A1 | 9/2012 |
| WO | 2015/018768 A1 | 2/2015 |

OTHER PUBLICATIONS

International Search Report for application No. PCT/US2018/013668 dated Mar. 21, 2018.
(Continued)

*Primary Examiner* — Justine R Yu
*Assistant Examiner* — Kelsey E Baller
(74) *Attorney, Agent, or Firm* — Artegis Law Group, LLP

(57) ABSTRACT

A flow control apparatus includes a pressure regulator fluidly coupled to an inlet region and an outlet region and configured to reduce a pressure from a first value in the inlet region to a second value in the outlet region, where the second value is lower than the first value; and a variable area orifice disposed between the outlet region and an outlet opening of the apparatus, wherein a flow rate of a gas is controlled by the variable area orifice and is discharged from the apparatus to a gas supply line. A free area of the variable area orifice that is disposed between a movable element and a surface of the variable area orifice is configured to change linearly in response to a translation of the movable element relative to the surface.

19 Claims, 7 Drawing Sheets

(51) Int. Cl.
*F16K 5/10* (2006.01)
*F16K 31/50* (2006.01)
*A61M 16/00* (2006.01)

(52) U.S. Cl.
CPC .......... *A61M 16/20* (2013.01); *A61M 16/201* (2014.02); *F16K 5/103* (2013.01); *F16K 31/508* (2013.01); *G05D 16/0608* (2013.01); *A61M 2016/0027* (2013.01)

(58) Field of Classification Search
CPC ........ A61M 16/107; A61M 2016/0027; A61M 5/16877; F16K 5/103; F16K 5/10; G05D 16/063; G05D 16/0636; G05D 16/0655
USPC .......... 16/206, 207; 128/205.24; 138/45, 46; 251/122
See application file for complete search history.

(56) References Cited

U.S. PATENT DOCUMENTS

| | | | |
|---|---|---|---|
| 2,973,007 A | 2/1961 | Schutmaat | |
| 3,204,657 A * | 9/1965 | Boyd | G05D 16/0663 137/484.8 |
| 3,426,794 A | 2/1969 | Freytag | |
| 3,561,466 A * | 2/1971 | Carden | A61M 16/208 137/102 |
| 4,211,386 A * | 7/1980 | Yocum | F16K 1/34 251/122 |
| 4,597,387 A * | 7/1986 | Carnegie | B63C 11/18 128/201.27 |
| 4,728,075 A * | 3/1988 | Paradis | F16K 1/52 251/122 |
| 5,002,050 A | 3/1991 | McGinnis | |
| 5,568,910 A * | 10/1996 | Koehler | A61M 16/1015 251/83 |
| 6,026,850 A * | 2/2000 | Newton | G05D 16/0655 137/505 |
| 6,237,594 B1 | 5/2001 | Davenport | |
| 7,337,805 B2 * | 3/2008 | Brown | F16K 7/14 137/625.33 |
| 8,485,213 B2 * | 7/2013 | Hawkins | G05D 16/0663 137/116.5 |
| 2004/0149949 A1 * | 8/2004 | Eriksson | A61M 16/20 251/186 |
| 2011/0168180 A1 * | 7/2011 | Lugtigheid | A61M 16/208 128/205.14 |
| 2012/0032101 A1 * | 2/2012 | Chen | A61M 16/20 251/337 |
| 2012/0272956 A1 | 11/2012 | Rusher | |
| 2017/0211714 A1 * | 7/2017 | Lei | G05D 16/0655 |
| 2018/0272100 A1 * | 9/2018 | Andersson | A61M 16/0677 |
| 2018/0299910 A1 * | 10/2018 | Inoue | G05D 16/0663 |

OTHER PUBLICATIONS

Non-Final Office Action received for U.S. Appl. No. 15/870,797, dated Apr. 6, 2020, 16 pages.

Non Final Office Action received for U.S. Appl. No. 15/870,797 dated Dec. 22, 2020, 12 pages.

* cited by examiner

REMOTE OXYGEN FLOW ADJUSTMENT

CROSS-REFERENCE TO RELATED APPLICATIONS

This application claims priority benefit of the United States Provisional Patent Application titled, "Remote Oxygen Cannula Flow Adjustment," filed on Jan. 13, 2017 and having Ser. No. 62/446,335. The subject matter of this related application is hereby incorporated herein by reference.

BACKGROUND OF THE INVENTION

Field of the Invention

The present invention relates generally to medical devices and, more specifically, to remote oxygen flow adjustment.

Description of the Related Art

Oxygen therapy is the standard of care for many patients with early to mid-stage lung diseases. In particular, individuals with chronic obstructive pulmonary disease (COPD), the third leading cause of death in the United States, are prescribed with oxygen therapy to increase blood oxygen saturation. Individuals that require such oxygen therapy typically have a centralized oxygen source within their home. Oxygen sources can be either liquid oxygen canisters, high-pressure oxygen cylinders, or oxygen concentrators.

Because state-of-the-art oxygen concentrators produce undesirable levels of noise and heat during operation, oxygen concentrators are typically maintained in a remote location within the home—usually in a different room than that occupied by the user. Similarly, liquid oxygen canisters and high-pressure oxygen cylinders are bulky and heavy, and typically remain in a fixed, out-of-the-way location. Therefore, to enable a user to move freely about the home, long segments of extension tubing (for example 25- or 50-foot lengths) are used to connect the user's nasal cannula to the home oxygen source. The use of extension tubing also allows oxygen sources to be placed in locations that are isolated from normal traffic areas in the home.

One drawback to remotely locating an oxygen source within a home or residence is that a user is usually a considerable distance away from the flow controls of the oxygen source, which prevents the user from being able to control the flow of oxygen from the oxygen source from his/her current location. This problem is exacerbated by the fact that oxygen needs are highly dependent on the user's current activity level, such as sitting, standing, or walking. For example, a typical user complaint is that the user needs to turn the source flow to an elevated level to enable the user to walk to a different location within the home, but then, once seated in the new location, the user needs to reduce the source flow to a lower level to reduce the nasal drying associated with an excess flow of oxygen. However, once the user has walked to the new location, he/she is not able to turn down the flow of oxygen without assistance from another person because the new location is usually located far away from the oxygen source, and the act of returning to the oxygen source to change the setting and then walking back to the seated location would require the undesired elevated flow setting. The user is left in a chicken-or-egg situation.

One solution for enabling remote adjustments to oxygen flow from an oxygen source is a flow control valve disposed near the inlet of a user's nasal cannula. By rotating a valve actuator, the user can increase or decrease the flow rate of oxygen entering the nasal cannula without having to walk back to the oxygen source. However, a drawback of such devices is the highly non-linear relationship between valve position and resulting flow rate, making accurate flow control settings very difficult for most users. For instance, when such a control valve is more than half open, large changes in valve position correspond to very little or no change in oxygen flow rate; whereas, when the control valve is mostly closed, small changes in valve position correspond to large changes in oxygen flow rate.

As the foregoing illustrates, what is needed in the art are more effective ways to enable oxygen flows from oxygen sources to be adjusted by users.

SUMMARY OF THE INVENTION

One embodiment of the present invention sets forth an apparatus for controlling air flow from a gas source. The apparatus includes a pressure regulator fluidly coupled to an inlet region and an outlet region and configured to reduce a pressure from a first value in the inlet region to a second value in the outlet region, where the second value is lower than the first value, and a variable area orifice disposed between the outlet region and an outlet opening of the apparatus, wherein a flow rate of a gas is controlled by the variable orifice area and is discharged from the apparatus to a gas supply line. A free area of the variable area orifice that is disposed between a movable element and a surface of the variable area orifice is configured to change linearly in response to a translation of the movable element relative to the surface.

At least one advantage of the technological improvements introduced by the disclosed design is that the flow rate of oxygen to a user from an oxygen source can be controlled by the user even when the oxygen source is located remotely from the user. A further advantage is that flow rates selected by the user are accurate, repeatable and controllable regardless of the outlet pressure of the oxygen source. Thus, a user can switch between oxygen sources, or an oxygen source can have variable output pressure, and a specific flow rate selected by the user remains the same. Yet another technological improvement of the disclosed design over prior art approaches is that a user can accurately vary flow rate in a linear fashion by rotating one portion of a flow control apparatus relative to another portion of the flow control apparatus.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following description, numerous specific details are set forth to provide a more thorough understanding of the embodiments of the present invention. However, it will be apparent to one of skill in the art that the embodiments of the present invention may be practiced without one or more of these specific details.

According to embodiments of the present invention, remote and accurate manual control of oxygen flow to a person receiving oxygen therapy (a "user") is enabled with a flow control apparatus disposed near the user. Specifically, the flow control apparatus is fluidly coupled to an outlet of an oxygen source and an inlet of an oxygen supply device for the user, such as a nasal cannula, and provides accurate and repeatable oxygen flow to the user independent of what oxygen source is used. Because the embodiments of the flow control apparatus enable the user to accurately and repeatably select a desired flow rate of oxygen without moving to the location of oxygen source, the benefits of oxygen therapy to the user are maximized or otherwise enhanced. One such embodiment is illustrated in FIG. 1.

Figure 1:
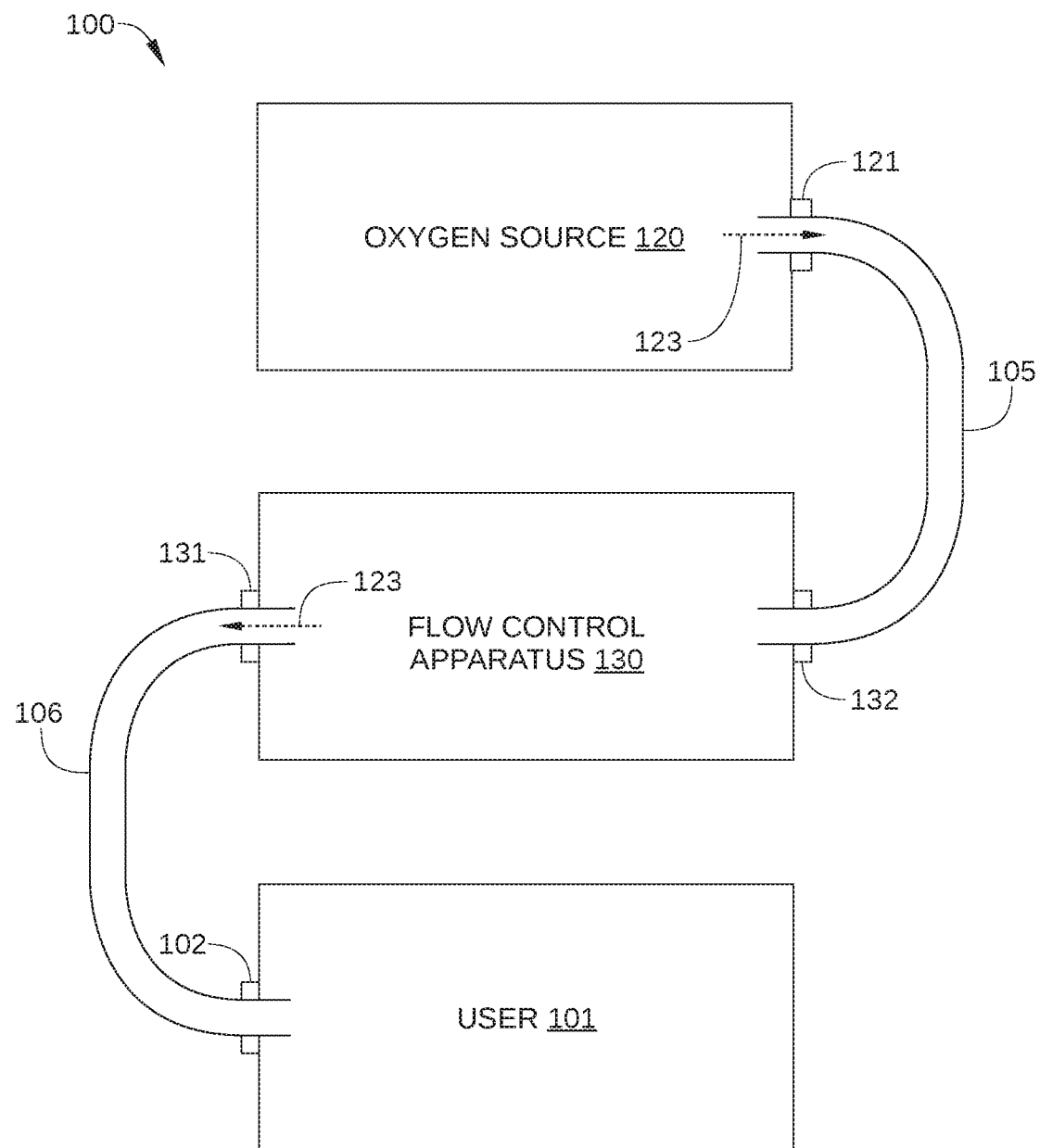
FIG. 1 is a block diagram of an oxygen therapy system configured to implement one or more aspects of the present invention.

FIG. 1 is a block diagram of an oxygen therapy system 100 configured to implement one or more aspects of the present invention. Oxygen therapy system 100 is configured to repeatably and accurately supply an oxygen-enriched gas 123 to a user 101 at a user-selectable flow rate. Oxygen therapy system 100 includes an oxygen source 120 and a flow control apparatus 130. As shown, an inlet 132 of flow control apparatus 130 is fluidly coupled to an outlet 121 of oxygen source 120, for example via a length of extension tubing 105. In addition, an outlet 131 of flow control apparatus 130 is fluidly coupled to an oxygen supply device 102 for user 101, such as a nasal cannula or face mask. Outlet 131 of flow control apparatus 130 can be fluidly coupled to oxygen supply device 102 via a length of extension tubing 106 that is typically much shorter than extension tubing 105. For example, the length of extension tubing 105 is typically selected to enable movement of user 101 throughout a home or at least throughout multiple adjacent rooms. By contrast, the length of extension tubing 106 is selected to enable user 101 to reach and manually operate flow control apparatus 130 without standing and/or walking to a different location.

Oxygen source 120 can be any apparatus configured to produce oxygen-enriched gas 123 for providing oxygen therapy to user 101. Oxygen source 120 can include an oxygen concentrator apparatus that employs any technically feasible oxygen concentration process to generate oxygen-enriched gas 123. For example, oxygen source 120 may be configured to employ a pressure swing adsorption (PSA) process, a rapid pressure swing adsorption (RPSA) process, a vacuum pressure swing adsorption (VPSA), or any other derivative process thereof. In each case, oxygen source 120 is configured to provide a targeted flow rate of oxygen-enriched gas 123 at a certain outlet pressure, for example on the order of 5 pounds-force per square inch gauge (PSIG). Alternatively or additionally, oxygen source 120 can include one or more liquid oxygen canisters or high-pressure oxygen cylinders. Liquid oxygen sources typically generate oxygen-enriched gas 123 at approximately 20 PSIG, and high-pressure gaseous cylinders are typically set at 50 PSIG. Thus, there is a wide range of possible outlet pressures for oxygen source 120.

For a particular flow-control setting, a conventional flow control device allows a different flow rate of oxygen-enriched gas 123 depending on the outlet pressure of oxygen source 120. According to embodiments of the present invention, for a particular setting, flow control apparatus 130 repeatably and accurately provides the same flow rate of oxygen-enriched gas 123 to oxygen supply device 102, regardless of the outlet pressure of oxygen source 120. One embodiment of flow control apparatus 130 is illustrated in FIG. 2.

Figure 2:
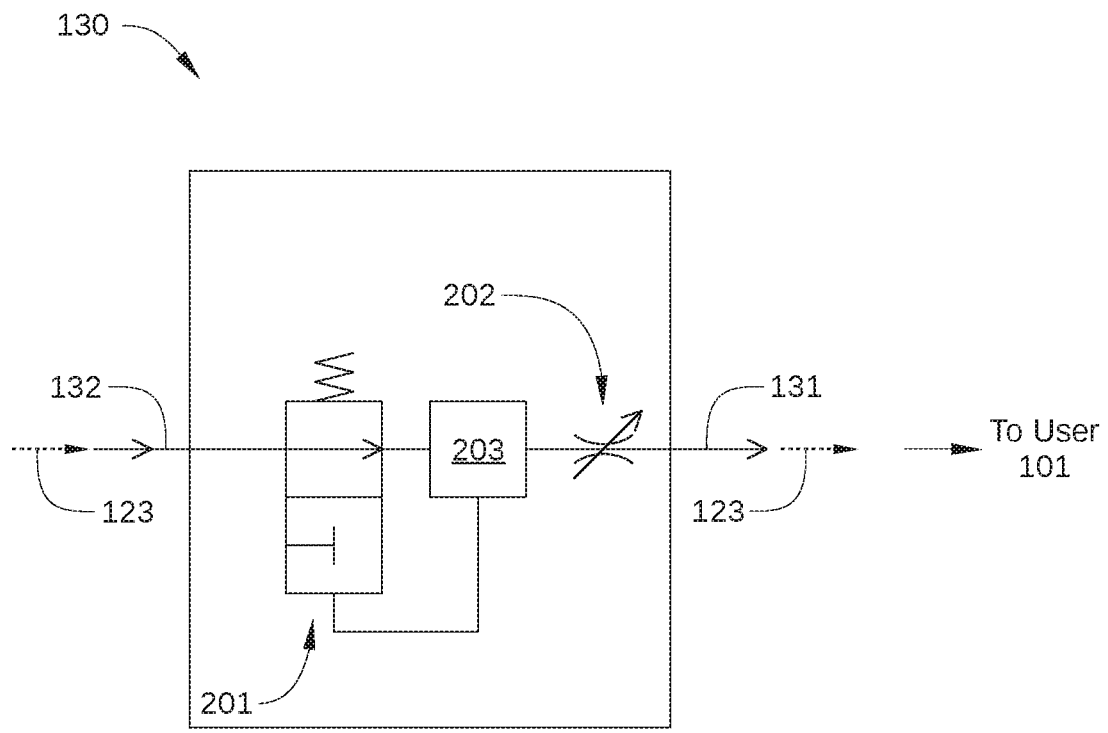
FIG. 2 is a more detailed illustration of the flow control apparatus of FIG. 1, according to various embodiments of the present invention.

FIG. 2 is a more detailed illustration of flow control apparatus 130, according to various embodiments of the present invention. Flow control apparatus 130 includes a pressure regulator 201 and a variable flow orifice 202 that is disposed downstream of pressure regulator 201. Pressure regulator 201 is configured to reduce the pressure of oxygen-enriched gas 123 entering flow control apparatus 130 at inlet 132 to a lower pressure. Specifically, pressure regulator 201 reduces the pressure of oxygen-enriched gas 123 to the lower pressure in an orifice inlet chamber 203 that is disposed upstream of variable flow orifice 202, where the orifice inlet chamber 203 is the same region as the outlet region of pressure regulator 201. Thus, pressure regulator 201 fixes the inlet pressure to variable flow orifice 202 to the lower pressure, regardless of the pressure of oxygen-enriched gas 123 at inlet 132. Generally, the lower pressure is selected to be less than the output pressure of oxygen sources that can be used with flow control apparatus 130, such as liquid oxygen canisters, high-pressure oxygen cylinders, or an oxygen concentrator. Therefore, pressure regulator 201 generally reduces the pressure of oxygen-enriched gas 123 to a pressure below about 5 PSIG, or even about 1 PSIG, to ensure that pressure regulator 201 does not interfere with the operation of an oxygen concentrator fluidly coupled to flow control apparatus 130.

As noted above, pressure regulator 201 fixes the inlet pressure to variable flow orifice 202 to a specific pressure, regardless of the pressure of oxygen-enriched gas 123 at inlet 132. Therefore, assuming that the flow path of oxygen-enriched gas 123 from variable flow orifice 202 to user 101 remains the same, then the flow rate of oxygen-enriched gas 123 through variable flow orifice 202 is a function of the free area of variable flow orifice 202. For example, as long as flow control apparatus 130 is fluidly coupled to user 101 via the same extension tubing 106 and the same oxygen supply device 102, the flow rate of oxygen-enriched gas 123 through variable flow orifice 202 is proportionate to the free area of variable flow orifice 202. As a result, the flow of oxygen-enriched gas 123 through variable flow orifice 202 can be repeatably and accurately set by user adjustments to the free area of variable flow orifice 202, regardless of the pressure of oxygen-enriched gas 123 entering flow control apparatus 130.

Variable flow orifice 202 is a user-settable flow control device that enables user 101 to accurately and repeatably set a flow rate of oxygen-enriched gas 123 without walking to the current location of oxygen source 120. For example, in some embodiments, a movable element of variable flow orifice 202, such as a pin or valve, is coupled to a threaded barrel included in variable flow orifice 202. As the threaded barrel is rotated, movement of the movable element relative to a valve seat increases or decreases the free area of variable flow orifice 202, which in turn increases or decreases the flow rate of oxygen-enriched gas 123 through variable flow orifice 202. Thus, in such embodiments, a user can manually adjust the flow rate of flow control apparatus 130 by rotating the threaded barrel. One such embodiment is illustrated in FIG. 3.

Figure 3:
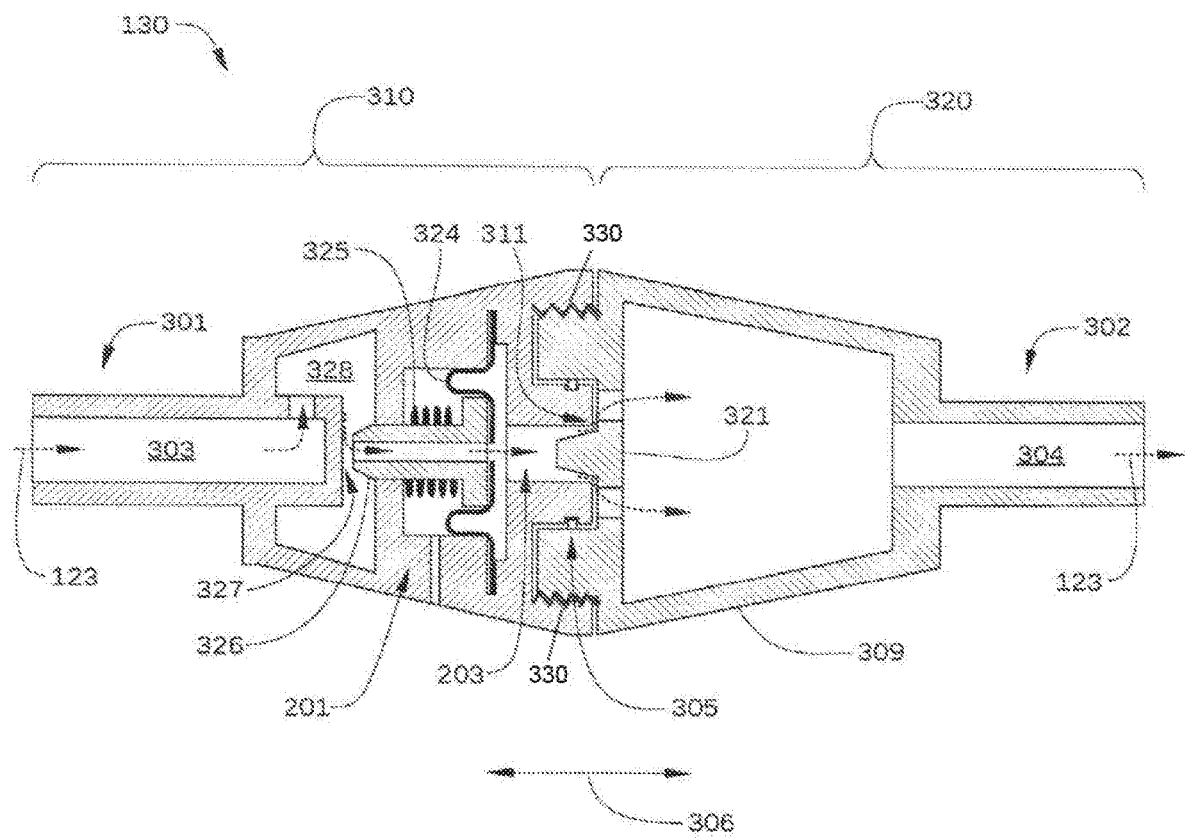
FIG. 3 is a cross-sectional illustration of the flow control apparatus of FIG. 2, according to various embodiments of the present invention.

FIG. 3 is a cross-sectional illustration of flow control apparatus 130, according to various embodiments of the present invention. In the embodiment illustrated in FIG. 3, flow control apparatus 130 includes an upstream body half 310 and a downstream body half 320 that are rotatably coupled to each other. In addition, flow control apparatus 130 includes attachment fittings 301 and 302 for attaching flow control apparatus 130 to extension tubing 105 and extension tubing 106, respectively. Flow control apparatus 130 further includes an inlet opening 303, an outlet opening 304, and a sealing element 305 that is disposed between upstream body half 310 and downstream body half 320. In some embodiments, graduated indicators (not visible in FIG. 3) are formed on an outer surface 309 of downstream body half 320, so that a user can readily determine what the current rotational setting of downstream body half 320 is relative to upstream body half 310.

In some embodiments, upstream body half 310 and downstream body half 320 are rotatably coupled to each other via a threaded interface 330. In such embodiments, as upstream body half 310 and downstream body half 320 are rotated with respect to each other, the rotating action causes a movable element 321 included in downstream body half 320 to translate axially (the directions denoted by arrows 306) toward or away from upstream body half 310. The axial translation of movable element 321 causes a flow area between movable element 321 and a seat 311 to increase or decrease, depending on the direction of rotation. It is noted that the flow area between movable element 321 and seat 311 is the free area of variable flow orifice 202.

In the embodiment illustrated in FIG. 3, movable element 321 translates axially relative to seat 311 because movable element 321 is included in or fixed to downstream body half 320 and seat 311 is included in or fixed to upstream body half 310. Therefore, variable flow orifice 202 is formed by the interface between upstream body half 310 and downstream body half 320. By contrast, pressure regulator 201 is included in upstream body half 310.

Pressure regulator 201 includes a diaphragm 324, a spring 325, and a poppet 326 that is configured to close against a seat 327. In operation, as pressure decreases below a target pressure in orifice inlet chamber 203, the force exerted by diaphragm 324 in opposition to spring 325 is reduced. As a result, spring 325 moves poppet 326 away from seat 327, and more oxygen-enriched gas 123 flows from a regulator inlet chamber 328 into orifice inlet chamber 203, thereby increasing the pressure in orifice inlet chamber 203 back up to the target pressure. Conversely, as pressure increases above a target pressure in orifice inlet chamber 203, the force exerted by diaphragm 324 in opposition to spring 325 is increased. As a result, poppet 326 moves toward seat 327, and the flow of oxygen-enriched gas 123 flowing from regulator inlet chamber 328 into orifice inlet chamber 203 is reduced while the flow exiting inlet chamber 203 continues through variable flow orifice 202, thereby decreasing the pressure in orifice inlet chamber 203 back down to the target pressure. Therefore, even when movable element 321 is translated away from seat 311 and the flow rate of oxygen-enriched gas 123 leaving orifice inlet chamber 203 increases, pressure regulator 201 compensates and maintains substantially the same pressure in orifice inlet chamber 203.

Because pressure regulator 201 maintains a substantially constant pressure in orifice inlet chamber 203 during operation of flow control apparatus 130, the flow rate of oxygen-enriched gas 123 through variable flow orifice 202 is directly proportional to the free area of variable flow orifice 202. As noted above, the free area of variable flow orifice 202 is increased and decreased by axial translation of movable element 321 that occurs in response to upstream body half 310 and downstream body half 320 being rotated with respect to each other. In the embodiment illustrated in FIG. 3, movable element 321 includes a tapered post and seat 311 has a fixed diameter opening. Thus, as movable element 321 translates axially along the directions indicated by arrows 306, a tapered surface of movable element 321 moves closer to or farther from the fixed opening of seat 311, and the free area of variable flow orifice 202 changes accordingly.

In some embodiments, movable element 321 and/or a surface of seat 311 is configured so that the free area of variable flow orifice 202 changes in direct proportion to axial translation of movable element 321. One such embodiment is illustrated in FIG. 4.

Figure 4:
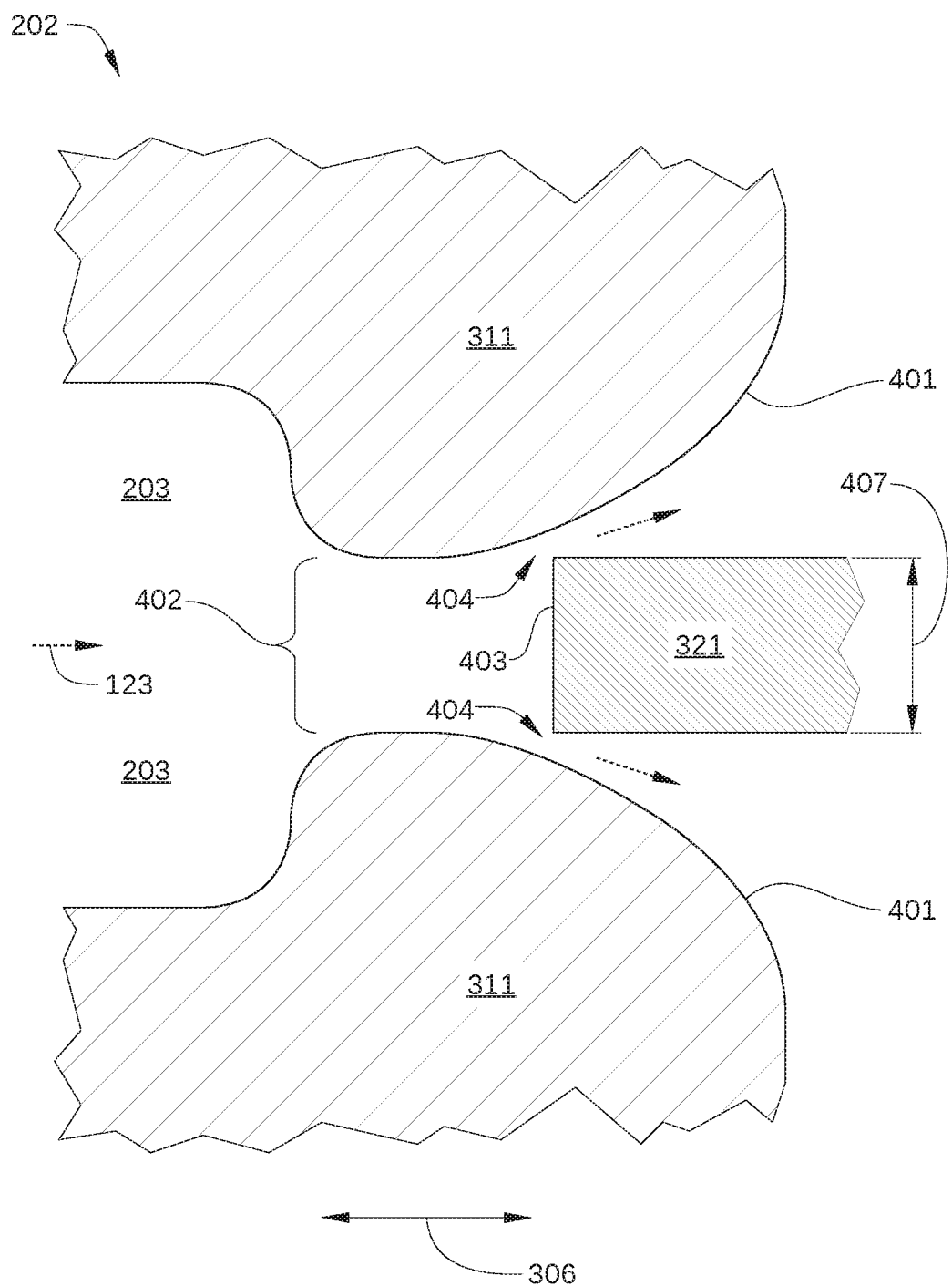
FIG. 4 is a cross-sectional illustration of the movable element and seat of the flow control apparatus of FIG. 2, according to various embodiments of the present invention.

FIG. 4 is a cross-sectional illustration of movable element 321 and seat 311, according to various embodiments of the present invention. In the embodiment illustrated in FIG. 4, seat 311 includes a curved surface 401 formed around a circular opening 402 that is fluidly coupled to orifice inlet chamber 203. An end 403 of movable element 321 that is proximate circular opening 402 has a diameter 407 and is aligned coaxially with circular opening 402, so that an annular free area 404 is disposed between movable element 321 and curved surface 401 of seat 311. When user 101 rotates downstream body half 320 relative to upstream body half 310 (see FIG. 3), for example clockwise, movable element 321 is displaced axially to the left in FIG. 4. As movable element 321 is displaced axially to the left and closer to curved surface 401 of seat 311, annular free area 404 decreases in direct proportion to the axial displacement of movable element 321. In embodiments in which upstream body half 310 and downstream body half 320 are coupled to each other via a threaded interface, axial displacement of movable element 321 is directly proportional to rotation of upstream body half 310 with respect to downstream body half 320. Consequently, in such embodiments, variation of annular free area 404 is also directly proportional to rotation of upstream body half 310 relative to downstream body half 320. As a result, evenly-spaced graduated indicators can be formed on outer surface 309 of body half 320 that accurately and repeatably indicate relative flow rate of oxygen-enriched gas 123 through flow control apparatus 130. One such embodiment is illustrated in FIG. 5.

Figure 5:
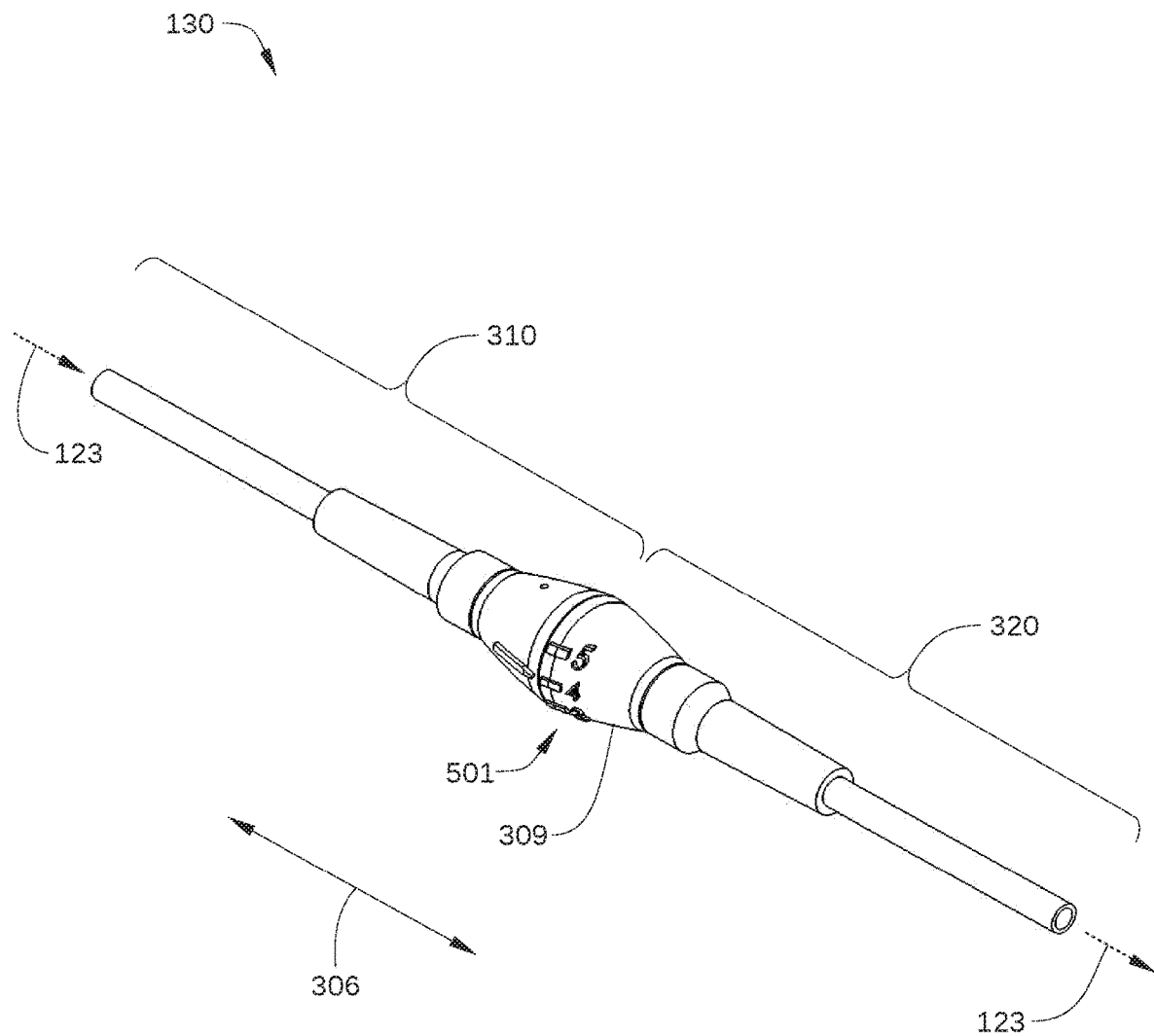
FIG. 5 is an external perspective view of the flow control apparatus of FIG. 2, according to various embodiments of the present invention.

FIG. 5 is an external perspective view of flow control apparatus 130, according to various embodiments of the present invention. In the embodiment illustrated in FIG. 5, graduated indicators 501 are formed on outer surface 309 of downstream body half 320, indicating the relative rotational position of upstream body half 310 to downstream body half 320. Graduated indicators 501 enable a user to easily determine what the current rotational setting of downstream body half 320 relative to upstream body half 310 is. As noted above, in some embodiments, variation of annular free area 404 (shown in FIG. 4) is directly proportional to the rotation of upstream body half 310 relative to downstream body half 320. In such embodiments, graduated indicators 501 provide accurate and repeatable feedback to user 101 as to the current flow rate of oxygen-enriched gas 123, regardless of what oxygen source is currently being employed in oxygen therapy system 100. In addition, in such embodiments, graduated indicators accurately reflect the relative flow rate of oxygen-enriched gas 123. For example, setting 4 corresponds to a flow rate that is twice that of setting 2.

In some embodiments, to effect the above-described change in annular free area 404 that is in direct proportion to the axial displacement of movable element 321, curved surface 401 is selected to have a particular profile. In such embodiments, curved surface 401 of seat 311 has the form of a continuously varying wall angle conical frustum. The particular profile of curved surface 401 is selected so that a change in axial position of end 403 of movable element 321 along the directions indicated by arrows 306 results in a proportional change in the annular free area 404. For example, if moving end 403 away from curved surface 401 for an axial distance X results in a change in area of annular free area 404 equal to ΔA, then moving end 403 away from curved surface 401 an axial distance 2X results in a change in area of annular free area 404 equal to 2ΔA. The profile of curved surface 401 may include circular, parabolic, elliptical, and/or exponential segments. In some embodiments, the profile of curved surface 401 can be determined using numerical methods known in the art. One method for determining a profile of curved surface 401 that results in a flow area change of an annular free area that is proportional to an axial positional change of a movable element is described in detail in U.S. Pat. No. 5,014,694, entitled "Ambient pressure air/oxygen blender."

Alternatively or additionally, in some embodiments, movable element 321 includes a curved surface that defines the size of annular free area 404. For example, rather than the conical cross-section of movable element 321 shown in FIG. 3, the cross-sectional profile of movable element 321 can be curved. In such embodiments, numerical methods known in the art can be employed to determine the profile of the curved cross-sectional profile of a surface of movable element 321 so that axial position change of movable element 321 results in a proportional change in annular free area 404.

Figure 6:
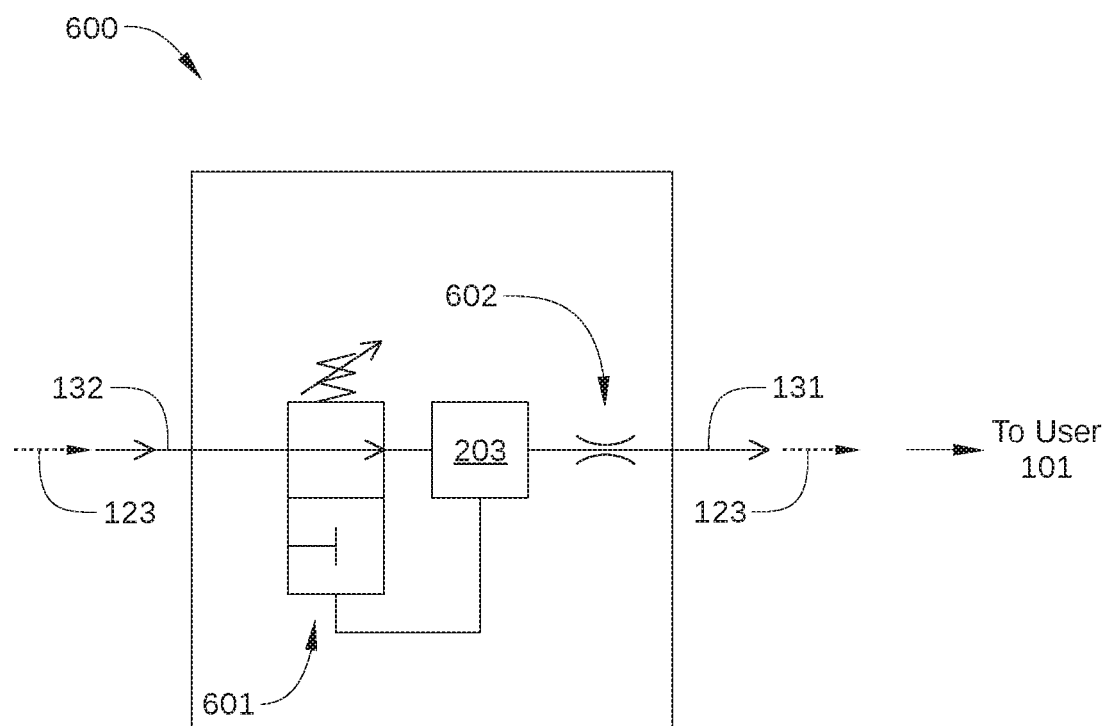
FIG. 6 is a more detailed illustration of a flow control apparatus, according to various embodiments of the present invention.

In some embodiments, a flow control apparatus includes a fixed orifice rather than a variable flow orifice, and flow rate of oxygen-enriched gas 123 is controlled with a user-adjustable pressure regulator. One such embodiment is illustrated in FIG. 6. FIG. 6 is a more detailed illustration of a flow control apparatus 600, according to various embodiments of the present invention. Flow control apparatus 600 includes a user-adjustable pressure regulator 601 and a fixed flow orifice 602 that is disposed downstream of user-adjustable pressure regulator 601. User-adjustable pressure regulator 601 is configured to reduce the pressure of oxygen-enriched gas 123 entering flow control apparatus 600 at inlet 132 to a lower pressure in orifice inlet chamber 203. Unlike flow control apparatus 130 of FIG. 2, flow control apparatus 600 controls the pressure in orifice inlet chamber 203 to a variable pressure. The variable pressure is selected based on a manual input from user 101, such as rotation of two body halves of flow control apparatus 600. The manual input changes the preload on a spring in user-adjustable pressure regulator 601, which effectively changes the regulated pressure present in orifice inlet chamber 203. Because the remainder of oxygen therapy system 100 between orifice inlet chamber 203 and user 101 is fixed, changes in pressure in orifice inlet chamber 203 can be employed to repeatably control flow rate of oxygen-enriched gas 123 for specific settings of the manual input.

Figure 7:
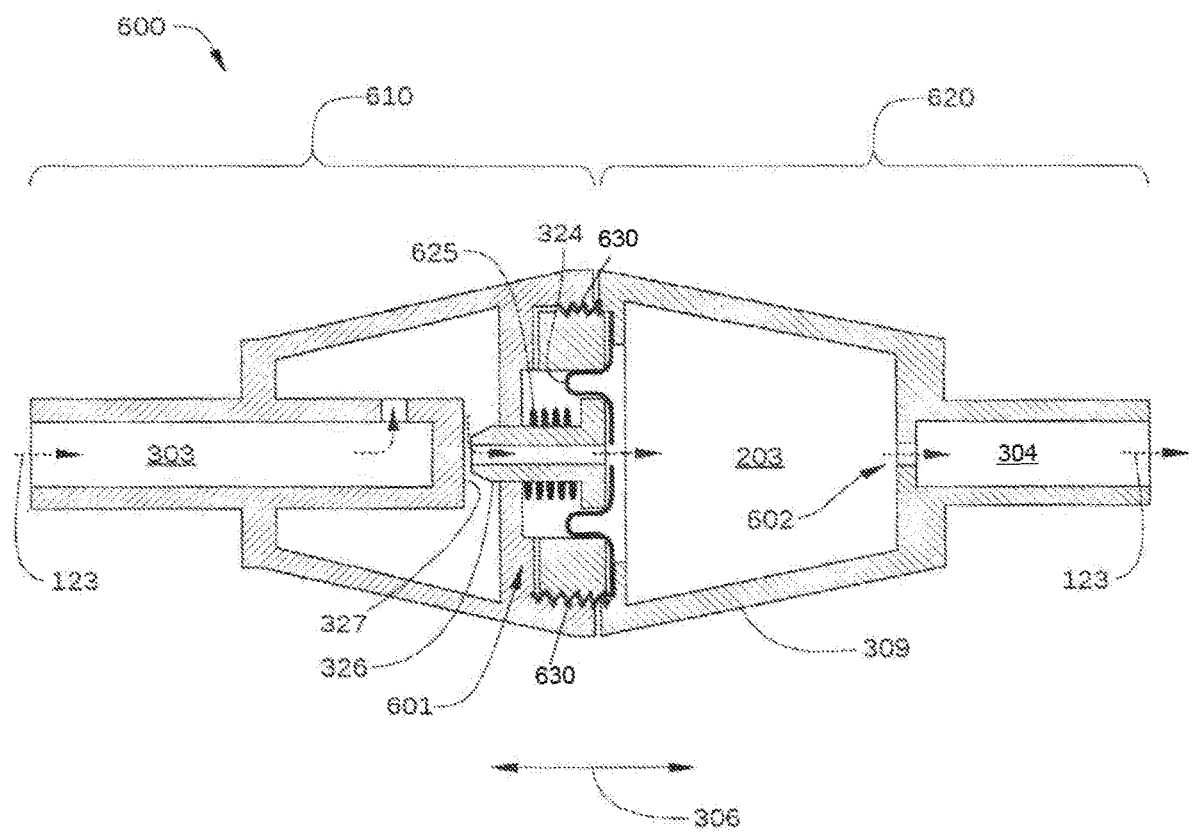
FIG. 7 is a cross-sectional illustration of the flow control apparatus of FIG. 6, according to various embodiments of the present invention.

In some embodiments, the manual input for changing the pressure in orifice inlet chamber 203 is rotation of two body halves of flow control apparatus 600 relative to each other. One such embodiment is illustrated in FIG. 7. FIG. 7 is a cross-sectional illustration of flow control apparatus 600, according to various embodiments of the present invention. Flow control apparatus 600 is substantially similar in configuration to flow control apparatus 130 of FIG. 3, except for the differences noted below.

Flow control apparatus 600 includes an upstream body half 610 and a downstream body half 620 that are rotatably coupled to each other via a threaded interface 630. As upstream body half 610 and downstream body half 620 are rotated with respect to each other, a threaded interface therebetween causes downstream body half 620 to translate axially (along the directions denoted by arrows 306) toward or away from upstream body half 610. The axial translation of downstream body half 620 causes more or less force to be exerted against poppet 326, which adjusts a preload force of an opening spring 625 in adjustable pressure regulator 601. The adjusted preload force effectively changes the regulated pressure in orifice inlet chamber 203, which in turn changes the flow rate of oxygen-enriched gas 123 through fixed flow orifice 602.

It is noted that adjustable pressure regulator 601 is partially disposed within upstream body half 610 and partially disposed within downstream body half 620. In the embodiment illustrated in FIG. 7, seat 327 and a portion of poppet 326 are disposed within upstream body half 610, diaphragm 324 is included within downstream body half 620, and opening spring 625 and the remainder of poppet 326 are disposed in a region between upstream body half 610 and downstream body half 620.

In alternative embodiments, fixed flow orifice 602 is disposed in a different location within flow control apparatus 600 than that shown in FIG. 6. For example, in some embodiments, the central opening of poppet 326 can be employed as fixed flow orifice 602. In such embodiments, the central opening of poppet 326 is configured with a smaller free area than other constrictions along the flow path of oxygen-enriched gas 123 through flow control apparatus. Any other suitable location for fixed flow orifice 602 can also be selected within flow control apparatus 600 without exceeding the scope of the invention.

In sum, embodiments of the present invention provide a flow control apparatus that includes a pressure regulator upstream of a flow control orifice. In some embodiments, the pressure regulator controls an inlet pressure to the flow control orifice to a fixed pressure and the flow control orifice is a variable flow orifice that is user adjustable. In other embodiments, the pressure regulator controls an inlet pressure to the flow control orifice to a user-selected pressure and the flow control orifice is a fixed flow orifice. In either case, the flow control apparatus can be disposed between an oxygen source and an oxygen supply device for a user, such as a nasal cannula, to control a flow rate of oxygen to the user.

At least one advantage of the technological improvements introduced by the disclosed design is that the flow rate of oxygen to a user from an oxygen source can be controlled by the user even when the oxygen source is located remotely from the user. A further advantage is that flow rates selected by the user are accurate and repeatable, regardless of the outlet pressure of the oxygen source. Thus, a user can switch between oxygen sources, or an oxygen source can have variable output pressure, and a specific flow rate selected by the user remains the same. Yet another technological improvement of the disclosed design over prior art approaches is that a user can accurately vary flow rate in a linear fashion by rotating one portion of a flow control apparatus relative to another portion of the flow control apparatus.

1. In some embodiments, an apparatus comprises: a pressure regulator fluidly coupled to an inlet region and an outlet region and configured to reduce a pressure from a first value in the inlet region to a second value in the outlet region, where the second value is lower than the first value; and a variable area orifice disposed between the outlet region and an outlet opening of the apparatus, wherein a flow rate of a gas is controlled by the variable area orifice and is discharged from the apparatus to a gas supply line, wherein a free area of the variable area orifice that is disposed between a movable element and a surface of the variable area orifice is configured to change linearly in response to a translation of the movable element relative to the surface.

2. The apparatus of clause 1, wherein the movable element translates relative to the surface in response to a rotation of a first body portion of the apparatus relative to a second body portion of the apparatus.

3. The apparatus of clauses 1 or 2, wherein the movable element is coupled to the first body portion.

4. The apparatus of any of clauses 1-3, wherein the first body portion has an external surface that includes graduated rotation indicators.

5. The apparatus of any of clauses 1-4, wherein the movable element has a constant diameter portion that is proximate the surface.

6. The apparatus of any of clauses 1-5, wherein the movable element translates along an axis of the movable element relative to the surface in response to a rotation of the first body portion of the apparatus relative to the second body portion of the apparatus.

7. The apparatus of any of clauses 1-6, further comprising an inlet opening that is coupled to a gas source and the inlet region and is configured to receive receiving the gas from the gas source.

8. The apparatus of any of clauses 1-7, wherein the second value is less than a minimum operating pressure of the gas source.

9. The apparatus of any of clauses 1-8, wherein the pressure regulator is configured to maintain the second value as a constant value independent of the first value.

10. The apparatus of any of clauses 1-9, wherein the variable area orifice comprises an outlet of the outlet region.

11. The apparatus of any of clauses 1-10, wherein the surface comprises an inner bore surface of the variable area orifice.

12. The apparatus of any of clauses 1-11, wherein, when viewed in cross-section along the axis of the movable element, the surface has a curved shape.

13. In some embodiments, a system comprises: a gas source; and a flow control apparatus fluidly coupled to an outlet of the gas source, the flow control apparatus comprising: a pressure regulator fluidly coupled to an inlet region and an outlet region and configured to reduce a pressure from a first value in the inlet region to a second value in the outlet region, where the second value is lower than the first value; and a variable area orifice disposed between the outlet region and an outlet opening of the apparatus, wherein a gas is discharged from the apparatus to a gas supply line, wherein a free area of the variable area orifice that is disposed between a movable element of the variable area orifice and a surface of the variable area orifice is configured to change linearly in response to a translation of the movable element relative to the surface.

14. The system of clause 13, wherein the movable element translates relative to the surface in response to a rotation of a first body portion of the apparatus relative to a second body portion of the apparatus.

15. The system of clauses 13 or 14, wherein the movable element is coupled to the first body portion.

16. The system of any of any of clauses 13-15, wherein the first body portion has an external surface that includes graduated rotation indicators.

17. The system of any of clauses 13-16, wherein the movable element translates along an axis of the movable element relative to the surface in response to a rotation of the first body portion of the apparatus relative to the second body portion of the apparatus.

18. The system of any of clauses 13-17, wherein the pressure regulator is configured to maintain the second value as a constant value independent of the first value.

19. The system of any of clauses 13-18, wherein the variable area orifice comprises an outlet of the outlet region.

20. The system of any of clauses 13-19, wherein the surface comprises an inner bore surface of the variable area orifice.

Any and all combinations of any of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

The invention has been described above with reference to specific embodiments. Persons of ordinary skill in the art, however, will understand that various modifications and changes may be made thereto without departing from the broader spirit and scope of the invention as set forth in the appended claims. For example, and without limitation, although many of the descriptions herein refer to devices, persons skilled in the art will appreciate that the systems and techniques described herein are applicable to other types of devices. The foregoing description and drawings are, accordingly, to be regarded in an illustrative rather than a restrictive sense.

What is claimed is:

1. An apparatus, comprising:
a pressure regulator fluidly coupled to an inlet region and an outlet region and configured to reduce a pressure from a first value in the inlet region to a second value in the outlet region, where the second value is lower than the first value; and
a variable area orifice disposed between the outlet region and an outlet opening of the apparatus, wherein a flow rate of a gas is controlled by the variable area orifice, and the gas flows through the variable area orifice and is discharged from the apparatus to a gas supply line, wherein the variable area orifice has a flow area through which the gas flows, wherein the flow area is disposed between a movable element and a surface of the variable area orifice, and wherein at least one of the surface or the movable element has a curved shape in a flow direction of gas through the variable area orifice, and the flow area is configured to change linearly based on the curved shape in response to a translation of the movable element relative to the surface.

2. The apparatus of claim 1, wherein the movable element translates relative to the surface in response to a rotation of a first body portion of the apparatus relative to a second body portion of the apparatus.

3. The apparatus of claim 2, wherein the movable element is coupled to the first body portion.

4. The apparatus of claim 2, wherein the first body portion has an external surface that includes graduated rotation indicators.

5. The apparatus of claim 2, wherein the movable element has a constant diameter portion that is proximate the surface.

6. The apparatus of claim 2, wherein the movable element translates along an axis of the movable element relative to the surface in response to a rotation of the first body portion of the apparatus relative to the second body portion of the apparatus.

7. The apparatus of claim 1, further comprising an inlet opening that is coupled to a gas source and the inlet region and is configured to receive the gas from the gas source.

8. The apparatus of claim 7, wherein the second value is less than a minimum operating pressure of the gas source.

9. The apparatus of claim 1, wherein the pressure regulator is configured to maintain the second value as a constant value independent of the first value.

10. The apparatus of claim 1, wherein the variable area orifice comprises an outlet of the outlet region.

11. The apparatus of claim 1, wherein the surface comprises an inner surface of the variable area orifice.

12. A system, comprising:
a gas source; and
a flow control apparatus fluidly coupled to an outlet of the gas source, the flow control apparatus comprising:
a pressure regulator fluidly coupled to an inlet region and an outlet region and configured to reduce a pressure from a first value in the inlet region to a second value in the outlet region, where the second value is lower than the first value; and
a variable area orifice disposed between the outlet region and an outlet opening of the flow control apparatus, wherein a gas flows through the variable area orifice and is discharged from the flow control apparatus to a gas supply line,
wherein the variable area orifice has a flow area through which the gas flows, wherein the flow area is disposed between a movable element of the variable area orifice and a surface of the variable area orifice, and wherein at least one of the surface or the movable element has a curved shape in a flow direction of gas through the variable area orifice, and the flow area is configured to change linearly based on the curved shape in response to a translation of the movable element relative to the surface.

13. The system of claim 12, wherein the movable element translates relative to the surface in response to a rotation of a first body portion of the flow control apparatus relative to a second body portion of the flow control apparatus.

14. The system of claim 13, wherein the movable element is coupled to the first body portion.

15. The system of claim 13, wherein the first body portion has an external surface that includes graduated rotation indicators.

16. The system of claim 13, wherein the movable element translates along an axis of the movable element relative to the surface in response to a rotation of the first body portion of the flow control apparatus relative to the second body portion of the flow control apparatus.

17. The system of claim 12, wherein the pressure regulator is configured to maintain the second value as a constant value independent of the first value.

18. The system of claim 12, wherein the variable area orifice comprises an outlet of the outlet region.

19. The system of claim 12, wherein the surface comprises an inner surface of the variable area orifice.

* * * * *